US010791969B2

(12) United States Patent
Schmelzeisen-Redeker et al.

(10) Patent No.: US 10,791,969 B2
(45) Date of Patent: Oct. 6, 2020

(54) METHOD AND SYSTEM FOR METHOD FOR DETERMINING A BLOOD GLUCOSE LEVEL FOR A PATIENT

(71) Applicant: Roche Diabetes Care, Inc., Indianapolis, IN (US)

(72) Inventors: Guenther Schmelzeisen-Redeker, Lorsch (DE); Nikolaus Schmitt, Heidelberg (DE); Christian Ringemann, Mannheim (DE)

(73) Assignee: ROCHE DIABETES CARE, INC, Indianapolis, IN (US)

( * ) Notice: Subject to any disclaimer, the term of this patent is extended or adjusted under 35 U.S.C. 154(b) by 538 days.

(21) Appl. No.: 15/627,846

(22) Filed: Jun. 20, 2017

(65) Prior Publication Data
US 2017/0319112 A1    Nov. 9, 2017

Related U.S. Application Data

(63) Continuation of application No. PCT/EP2015/079628, filed on Dec. 14, 2015.

(30) Foreign Application Priority Data

Dec. 23, 2014    (EP) .................................... 14200205

(51) Int. Cl.
*A61B 5/145*        (2006.01)
*G16H 40/63*        (2018.01)
(Continued)

(52) U.S. Cl.
CPC ........ *A61B 5/14532* (2013.01); *A61B 5/1451* (2013.01); *A61B 5/6801* (2013.01);
(Continued)

(58) Field of Classification Search
None
See application file for complete search history.

(56) References Cited

U.S. PATENT DOCUMENTS 8,834,366 B2 *   9/2014   Hayter ..................... A61B 5/01
                                                              600/365
2007/0016381 A1 * 1/2007   Kamath ............. A61B 5/14532
                                                              702/19

(Continued)

FOREIGN PATENT DOCUMENTS

EP         1 528 891 A1    5/2005
WO    WO 2011/051922 A2    5/2011
(Continued)

OTHER PUBLICATIONS

Barcelo-Rico "Multimodel Approaches for Plasma Glucose Estimation in Continuous Glucose Monitoring Development of New Calibration Algorithms", Thesis, Apr. 1, 2012, Universtat Politecnica de Valencia, retrieved from internet: https://riunet.upv.es/bitstream/handle/10251/17173/tesisUPV3821.pdf on Apr. 4, 2016.
(Continued)

*Primary Examiner* — Michael R Bloch
(74) *Attorney, Agent, or Firm* — Woodard, Emhardt, Henry, Reeves & Wagner, LLP

(57) ABSTRACT

The present disclosure refers to a method for determining a blood glucose level for a patient, the method comprising detecting a present sensor signal in a present continuous interstitial blood glucose measurement for a patient; providing measurement data representing the present sensor signal; providing sensor signal correction data representing a patient-specific signal correction, the sensor signal correction data being determined from a former interstitial blood glucose measurement for the patient and comprising at least one of time delay data representing a patient-specific time delay $\Delta t$ between a blood glucose value measured in a
(Continued)

continuous interstitial blood glucose measurement and a blood glucose reference value measured in a capillary blood glucose measurement, and sensor sensitivity data representing, for the patient, a patient-specific sensor sensitivity for the sensor, determining corrected measurement data representing a corrected present sensor signal by applying the sensor signal correction data to the present sensor signal; and determining a blood glucose level for the patient from the corrected measurement data.

8 Claims, 9 Drawing Sheets

(51) Int. Cl.
| | | |
|---|---|---|
| *G06F 19/00* | (2018.01) | |
| *A61B 5/00* | (2006.01) | |
| *A61M 5/172* | (2006.01) | |
| *G16H 50/50* | (2018.01) | |
| *A61B 5/1473* | (2006.01) | |
| *A61B 5/1495* | (2006.01) | |
| *A61M 5/142* | (2006.01) | |

(52) U.S. Cl.
CPC .......... *A61M 5/1723* (2013.01); *G06F 19/00* (2013.01); *G16H 40/63* (2018.01); *A61B 5/002* (2013.01); *A61B 5/1473* (2013.01); *A61B 5/1495* (2013.01); *A61B 5/4839* (2013.01); *A61B 5/7221* (2013.01); *A61B 5/742* (2013.01); *A61M 5/14244* (2013.01); *G16H 50/50* (2018.01)

(56) References Cited

U.S. PATENT DOCUMENTS

2009/0112478 A1* 4/2009 Mueller, Jr. ....... A61B 5/14532
702/19
2010/0081909 A1* 4/2010 Budiman ........... A61B 5/14532
600/365
2012/0283542 A1 11/2012 McGarraugh
2013/0178727 A1* 7/2013 Hayter ............... A61B 5/14532
600/365

FOREIGN PATENT DOCUMENTS

| WO | WO 2012/108938 A1 | 8/2012 |
| WO | WO 2014/052136 A1 | 4/2014 |
| WO | WO 2014/128638 A1 | 8/2014 |

OTHER PUBLICATIONS

International Application No. PCT/EP2015/079628 International Search Report and Written Opinion of the International Searching Authority, dated Apr. 20, 2016.
Keenan et al. "Interstitial fluid glucose time-lag correction for real-time continuous glucose monitoring", Biomedica; Signal Processing and Control, vol. 8, No. 1, Jan. 1, 2013, pp. 81-89, XP055183760, ISSN: 1746-8094, DOI: 10.1016/j.bspc.2012.05.007 pp. 81-85.
Rossetti et al. "Estimating Plasma Glucose from Interstitial Glucose: The Issue of Calibration Algorithms in Commercial Continuous Glucose Monitoring Devices", Sensors, vol. 10, No. 12, Dec. 3, 2010, pp. 10936-10952, XP055135973, DOI: 10.3390/s10121936 pp. 10941-10947.
Schmelzeisen-Redeker et al. "Time Delay of CGM Sensors: Relavance, Causes, and Countermeasures", Journal of Diabetes Science and Technology, vol. 9, No. 5, Sep. 1, 2015, pp. 1006-1015, XP055244485, US ISSN: 1932-2968, DOI: 10.1177/1932296815590154.
Schmelzeisen-Redeker et al."845-P: Patient-Specific Effects on the Time Delay of a Novel CGM Sensor", Diabetes, vol. 63, No. Suppl. 1, Jun. 1, 2014, pp. A215-A216, XP055244514, abstract.
Youssef et al. "Continuous Glucose Monitoring in Subjects with Type I Diabetes: Improvement in Accuracy by Correcting for Background Current", Diabetes Technology & Therapeutics, vol. 12, No. 11, Nov. 1, 2010, pp. 921-928, XP055184275, DOI: 10.1089/dia.2010.0020 pp. 922-923.

* cited by examiner

METHOD AND SYSTEM FOR METHOD FOR DETERMINING A BLOOD GLUCOSE LEVEL FOR A PATIENT

CROSS-REFERENCE TO RELATED APPLICATION

This application is a Continuation of Application No. PCT/EP2015/079628, filed Dec. 14, 2015, which claims the benefit of European Application No. 14 200 205.4, filed Dec. 23, 2014, the entire disclosures of which are hereby incorporated by reference.

BACKGROUND

The invention relates to a method and a system for determining a blood glucose level for a patient. In general, such methods and systems are used in order to determine characteristics of patients' measured blood glucose values. The objective is to give the patient as well as the attending medical staff information which enable the patient to deal with his blood glucose values in an improved and appropriate manner. The blood glucose level may be determined by different measurement methods known as such. For example, the blood glucose level may be measured by means of an interstitial glucose sensor. Such sensor may be applied in a continuous measurement regime. Also, the blood glucose level may be determined by analysing a capillary blood sample.

For people suffering from diabetes it is especially important to keep their blood glucose values constantly at a particular level. A precondition for this is knowledge of their blood glucose value which is therefore measured using a blood glucose measuring device set up for this purpose. Blood glucose measuring devices are known in various embodiments.

If it is determined, on the basis of the measured values, that the blood glucose value has exceeded the target range, medicine is administered, for example by means of insulin injection or the oral administration of Metformin, an oral antidiabeticum. If the blood glucose values fall below the ideal or recommended level, sugar must be orally ingested, for example through food or drink. If the ideal level is exceeded for an extended period of time, there is the risk of serious health complications such as blindness, kidney damage, amputation of limbs or neuropathy. Very high short-term blood glucose levels can lead to nausea, dizziness, sweating or even conditions of confusion. Thus, it is particularly important for a patient with diabetes to know his blood glucose values at all times so that he is able to implement the appropriate measures to avoid the blood sugar values deviating from the target range.

Blood glucose values for a patient may be determined according to a continuous measurement regime. Such measurements are also known as CGM measurements (Continuous Glucose Monitoring). In this process, the blood glucose values are measured e.g. every minute such that, for example, the progress of the blood glucose value can be collected over an entire day or longer. This allows the determination of short-term or medium-term trends in blood glucose progression and the identification of patterns of blood glucose variations over the day. It also allows to detect in real-time dangerous situations of a patient with diabetes (e.g. hypoglycaemia) and to warn or alarm the patient, respectively.

CGM is usually performed by measuring glucose in the interstitial space of adipose tissue as a surrogate for the glucose level in blood. It has been observed that there is a time delay (time lag) between the interstitial glucose concentration measured with a continuous glucose measurement using an interstitial sensor and the glucose measurement from capillary blood. A blood glucose level change determined from a capillary blood analysis will be observed delayed in the interstitial glucose measurement. Such time lag may have great influence on utilising the data of a CGM sensor. For example, a large time lag results in a delayed warning signal on passing a glucose threshold for hypoglycaemia. The performance data of a CGM sensor are also affected by the time lag: for example large time lag leads to poorer mean ARD (Absolute Relative Difference) values when CGM data are compared to reference blood glucose values, even if the raw data quality is very good and interstitial glucose measurement is accurate. In addition, methods of (partially) correcting the time lag are affected by the current time lag.

It was proposed to apply a mean time lag $\Delta tm$ between blood and interstitial glucose assumed to be identical for all patients for the correction of the actually measured interstitial glucose value in order to estimate the actual glucose value in capillary blood. Knowing the momentary CGM value $I(t)$ and its rate of change $dI/dt$, the CGM glucose value in Atm minutes can be estimated by the formula: $I(t+\Delta t)=I(t)+dI/dt*\Delta t$. This represents the estimation of the actual capillary blood glucose level. In the scientific literature quite different values have been published for the time lag detected for interstitial sensors of the same type, e.g. from about 5 to about 20 minutes depending on the sensor type. Even greater is the reported range of individual time lags of interstitial sensors of different type, which can be up to 40 minutes.

SUMMARY

It is the object to provide improved technologies for determining a blood glucose level for a patient from a continuous interstitial blood glucose measurement.

According to the present disclosure a method and a system for determining a blood glucose level for a patient according to claims 1 and 9, respectively, are provided. Further developments are disclosed in dependent claims.

According to one aspect, a method for determining a blood glucose level for a patient is provided, the method comprising, in a system for determining the blood glucose level for the patient: detecting a present sensor signal in a present continuous interstitial blood glucose measurement for a patient; providing measurement data representing the present sensor signal; providing sensor signal correction data representing, for the patient, a patient-specific signal correction, the sensor signal correction data being determined from a former interstitial blood glucose measurement for the patient and comprising at least one of (i) time delay data representing, for the patient, a patient-specific time delay $\Delta t$ between a blood glucose value measured in a continuous interstitial blood glucose measurement and a blood glucose reference value measured in a capillary blood glucose measurement, the blood glucose value and the blood glucose reference value referring to the same blood glucose level, (ii) sensor offset data representing, for the patient, a patient-specific sensor signal offset for the sensor, and (iii) sensor sensitivity data representing, for the patient, a patient-specific sensor sensitivity for the sensor; determining corrected measurement data representing a corrected present sensor signal by applying the sensor signal correction data to the present sensor signal; and determining a blood glucose level for the patient from the corrected measurement data.

According to another aspect, a system for determining a blood glucose level for a patient is provided, the system comprising a blood glucose measurement device, and a an analyzing device. The blood glucose measurement device is configured to detect a present sensor signal in a present continuous interstitial blood glucose measurement for a patient. The an analyzing device, comprising a data processing device, is configured to provide sensor signal correction data representing, for the patient, a patient-specific signal correction. The sensor signal correction data are determined from a former interstitial blood glucose measurement for the patient and comprising at least one of (i) time delay data representing, for the patient, a patient-specific time delay $\Delta t$ between a blood glucose value measured in a continuous interstitial blood glucose measurement and a blood glucose reference value measured in a capillary blood glucose measurement, the blood glucose value and the blood glucose reference value referring to the same blood glucose level, (ii) sensor offset data representing, for the patient, a patient-specific sensor signal offset for the sensor, and (iii) sensor sensitivity data representing, for the patient, a patient-specific sensor sensitivity for the sensor. The analyzing device is further configured to provide corrected measurement data representing a corrected present sensor signal by applying the sensor signal correction data to the present sensor signal; and a blood glucose level for the patient from the corrected measurement data.

Applying an individual patient-specific signal correction does improve the accuracy of determining the patient's blood glucose level with the continuous interstitial blood glucose measurement. Inaccuracy caused by the application of a mean correction value is eliminated. Technologies for a personalized determination of the blood glucose level are provided.

The sensor signal correction data may be determined from a former continuous interstitial blood glucose measurement and/or a former clinical controlled interstitial blood glucose measurement for the patient. Blood glucose measurement data gathered before the present measurement are analyzed for the patient retrospectively. Determination of the sensor signal correction data may be performed for a plurality of sets of measurement data from different former interstitial blood glucose measurements for the patient. Thereby, with regard to the sensor signal correction data the variance may be reduced.

With regard to determining the sensor signal correction data providing for the patient-specific signal correction, from the former interstitial blood glucose measurements measurement data may be selected which comprise fluctuations or variations of the blood glucose level of at least 0.5 mg/dl×min. With regard to fluctuations or variations of the blood glucose level, an upper limit may be set, for example, at 3 mg/dl×min. In response to providing data for the former interstitial blood glucose measurement(s) the data being indicative of the patient's blood glucose level may be screened for subset(s) of data comprising such fluctuations or variations.

The sensor signal correction data may be determined from measurement data selected to comprise fluctuations or variations of the patient's blood glucose level of 0.5 to 3 mg/dl×min, wherein sensor signals (measurement data) are collected every 5 to 20 min. As an alternative, the sensor signal correction data may be determined from measurement data selected to comprise fluctuations or variations of the patient's blood glucose level of 0.5 to 1.5 mg/dl×min, wherein sensor signals (measurement data) are collected every 10 to 20 min. Further, the sensor signal correction data may be determined from measurement data selected to comprise fluctuations or variations of the patient's blood glucose level of 0.5 to 1 mg/dl×min, wherein sensor signals (measurement data) are collected every 15 to 20 min.

Prior to the step of providing the sensor offset data, the patient-specific sensor signal offset for the sensor is determined in a measurement allowing observation of the patient-specific sensor offset. Such patient-specific sensor signal offset may be determined for a single interstitial sensor type and/or a group of interstitial sensor being of different type, but showing similar offset for the patient under investigation. The sensor signal offset refers to a so-called zero current representing a sensor signal (current) detected, for the patient, independently of the blood glucose level.

Although applying both the patient-specific time delay and the patient-specific sensor signal offset in the method for determining the blood glucose level of a patient will provide enhanced improvement, the patient-specific sensor signal offset may be applied without accounting for the patient-specific time delay or lag. Still, it will improve precision of the individual blood glucose determination.

Prior to the step of providing the sensor sensitivity data, the patient-specific sensor sensitivity for the sensor may be determined in a measurement allowing observation of the patient-specific sensor sensitivity. Such patient-specific sensor sensitivity may be determined for a single interstitial sensor type and/or a group of interstitial sensor being of different type, but showing similar sensor sensitivity for the patient under investigation. The application of the patient-specific sensor sensitivity will provide for improved individualized blood glucose level determination.

In an embodiment, with regard to the sensor sensitivity, the sensor measures an electrical current which is indicative for the glucose concentration in the interstitial fluid around the sensor in the adipose tissue. The sensor current is proportional to the glucose concentration. The slope of the sensor current vs. glucose line may be referred to as sensitivity of the sensor (how much current is detected per unit concentration of glucose). More generally, the sensor sensitivity is the minimum input of the physical parameter (concentration of glucose) that will cause a detectable output change (current change) of the sensor, also referred to as $\Delta y/\Delta x$ or $dy/dx$. The patient-specific sensor sensitivity may be determined from the slope of the continuously detected sensor signal.

The intercept of the line with the y-axis (sensor current) is the offset current (=the sensor current when glucose concentration is zero). Obviously one can determine the same set of parameters from sensor current vs. time and the glucose line vs. time.

With respect to the patient-specific sensor sensitivity, application in combination with the patient-specific sensor signal offset and/or the patient-specific time delay in the method for determining the blood glucose level of a patient will provide enhanced improvement of the personalized blood glucose level determination. As an alternative, the patient-specific sensor sensitivity correction may be applied without accounting for the other patient specific corrections. Still, it will improve precision of the individual blood glucose determination.

In case a combined individualized glucose level determination is performed, the determinations may be done in the following order: first the patient-specific time lag is determined and corrected for, secondly the patient-specific sensor signal offset is determined and corrected for, and lastly the patient-specific sensor sensitivity is determined and corrected for. The determined set of parameters is then used in e.g. converting continuously measured sensor signals to corresponding glucose levels. The conversion may be performed continuously.

In the method, the applying the sensor signal correction data to the present sensor signal further may comprise, in the system for determining the blood glucose level, applying the time delay data. The applying may comprise detecting the present sensor signal at a measuring time tm in the present continuous interstitial blood glucose measurement for the patient; and determining blood glucose level data representing a previous blood glucose level of the patient at a previous time tpr=tm−Δt by determining a blood glucose value from the measurement data and assigning the blood glucose value to the previous time tpr.

The method may further comprise providing rate of change data representing a rate of change of the blood glucose level of the patient, and providing present blood glucose level data representing a present blood glucose level of the patient at the measuring time tm by determining a present blood glucose value from the blood glucose value at the previous time tpr and the rate of change of the blood glucose level. The rate of change indicates the change of the patient's blood glucose level over time. This information can be used for determining the change over a time period from tpr to tm. Starting from the blood glucose level at the previous time tpr, the blood glucose level of the patient at the present time tm can be determined.

The method may further comprise, in the system for determining the blood glucose level, providing rate of change data representing a rate of change of the blood glucose level of the patient, and providing future blood glucose level data representing a future blood glucose level of the patient at a future time tf=tm+Δt by determining a future blood glucose value from the blood glucose value at the previous time tpr and the rate of change of the blood glucose level. The rate of change indicates the change of the patient's blood glucose level over time. This information can be used for determining the change over a time period between tpr and tf or, as an alternative, a time period between tm and tf. Starting from the blood glucose level at the previous time tpr or at the measuring time tm, the blood glucose level of the patient at the present time tm is determined.

The applying of the sensor signal correction data to the present sensor signal may further comprise subtracting the patient-specific sensor signal offset from the present sensor signal.

The method may further comprise
  providing pre-set sensor signal correction data in a memory device of the system for determining the blood glucose level, the pre-set sensor signal correction data representing, for the sensor, a pre-set sensor-specific signal correction, and comprising at least one of pre-set sensor offset data, and pre-set sensor sensitivity data;
  determining whether the sensor signal correction data are different from the pre-set sensor signal correction data; and
  applying the sensor signal correction data to the present sensor signal if the sensor signal correction data are determined to be different from the pre-set sensor signal correction data, otherwise applying the pre-set sensor signal correction data to the present sensor signal.

The pre-set sensor signal correction data may provide for sensor-specific parameters characterizing individual characteristics of the sensor to be used for the measurement. The pre-set sensor signal correction data may be stored in the memory prior to the measurement, e.g. in the course of a calibration process or at the time of connecting the sensor to the system for determining the blood glucose level.

The determining whether the sensor signal correction data are different from the pre-set sensor signal correction data may further comprise determining a difference value for the sensor signal correction data and the pre-set sensor signal correction data; and determining the sensor signal correction data to be different from the pre-set sensor signal correction data if the difference value is equal to or bigger than a pre-set difference value. The pre-set difference value may be a relative value identifying a relative difference between the data, e.g. the pre-set difference value may be provided as percent value. For example, the pre-set difference value may identify a value of 10%, indicating that the sensor signal correction data shall be determined different from the pre-set sensor signal correction data if there is a difference of at least 10%. As an alternative, the pre-set difference value may identify a value of 20%.

The method may further comprise, if the sensor signal correction data are determined to be different from the pre-set sensor signal correction data, replacing the pre-set sensor signal correction data in the memory device by the sensor signal correction data in the memory device. The pre-set sensor signal correction data may be overwritten by the sensor signal correction data in the memory. The replacing may apply to at least one of the pre-set sensor offset data, and the pre-set sensor sensitivity data.

In a similar way pre-set patient-specific time delay may be stored in the memory, but overwritten afterwards, e.g. during a measurement process and/or a (additional) calibration process.

In an alternative method for determining a blood glucose level for a patient, the method is comprising: detecting a present sensor signal at a measuring time tm in a present continuous interstitial blood glucose measurement for a patient; providing measurement data representing the present sensor signal in a data processing system; providing time delay data representing, for the patient, a patient-specific time delay Δt between a blood glucose value measured in a continuous interstitial blood glucose measurement and a blood glucose reference value measured in a capillary blood glucose measurement in the data processing system, the blood glucose value and the blood glucose reference value referring to the same blood glucose level; and providing blood glucose level data representing a previous blood glucose level of the patient at a previous time tpr=tm−Δt by determining a blood glucose value from the measurement data and assigning the blood glucose value to the previous time tpr in the data processing system.

According to an alternative embodiment, a system for determining a blood glucose level for a patient is provided, the system comprising: a blood glucose measurement device configured to detect a present sensor signal at a measuring time tm in a present continuous interstitial blood glucose measurement for a patient; and an analyzing device comprising a data processing device. The data processing device is configured to provide measurement data representing the present sensor signal; time delay data representing, for the patient, a patient-specific time delay Δt between a blood glucose value measured in a continuous interstitial blood glucose measurement and a blood glucose reference value measured in a capillary blood glucose measurement in the data processing system, the blood glucose value and the blood glucose reference value referring to the same blood glucose level; and blood glucose level data representing a previous blood glucose level of the patient at a previous time tpr=tm−Δt by determining a blood glucose value from the measurement data and assigning the blood glucose value to the previous time tpr.

With regard to the method, in the data processing system, the following may be provided: providing rate of change data representing a rate of change of the blood glucose level of the patient, and providing present blood glucose level data representing a present blood glucose level of the patient at the measuring time tm by determining a present blood glucose value from the blood glucose value at the previous time tpr and the rate of change of the blood glucose level.

In the data processing system, the method may comprise providing rate of change data representing a rate of change of the blood glucose level of the patient, and providing future blood glucose level data representing a future blood glucose level of the patient at a future time tf=tm+Δt by determining a future blood glucose value from the blood glucose value at the previous time tpr and the rate of change of the blood glucose level.

Further, in the data processing system, the method may comprise providing sensor offset data representing, for the patient, a patient-specific sensor signal offset for the sensor, and determining corrected measurement data representing a corrected present sensor signal by subtracting the patient-specific sensor signal offset from the present sensor signal.

As an alternative, in the data processing system, the method may comprise providing sensor sensitivity data representing, for the patient, a patient-specific sensor sensitivity for the sensor, and determining corrected measurement data representing a corrected present sensor signal by applying the patient-specific sensor sensitivity to the present sensor signal.

The data processing system may be provided in a blood glucose control device configured to continuously monitor the blood glucose level of a user. Different embodiments for blood glucose control devices as such are known in the art.

BRIEF DESCRIPTION OF THE DRAWINGS

Following, embodiments, by way of example, are described with reference to figures. In the figures show.

DESCRIPTION OF THE SELECTED EMBODIMENTS

Figure 1:
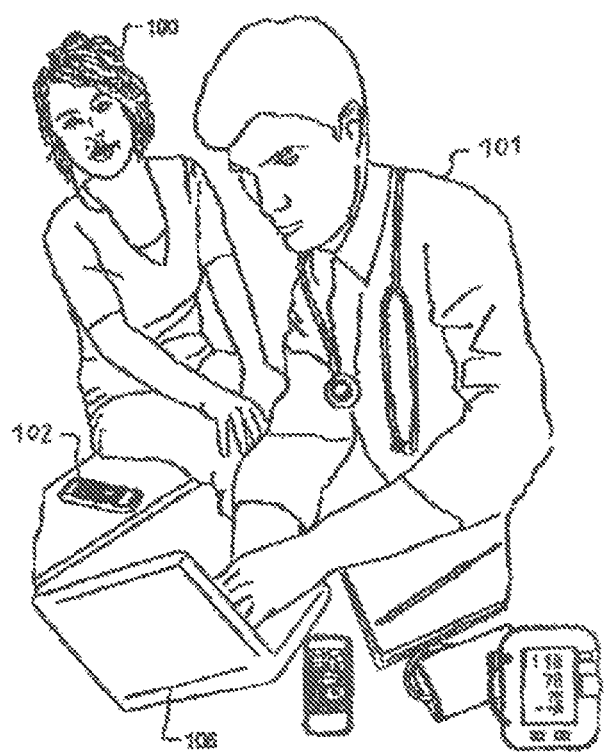
FIG. 1 a schematic representation of a patient and a treating clinician.

Referring now to FIG. 1, a person 100 with diabetes and a healthcare professional 101 are shown in a clinical environment. Persons with diabetes include persons with metabolic syndrome, pre-diabetes, type 1 diabetes, type 2 diabetes, and gestational diabetes and are collectively referred to as a patient. Healthcare providers for diabetes are diverse and include nurses, nurse practitioners, physicians, and endocrinologists and are collectively referred to as a clinician.

During a healthcare consultation, the patient 100 typically shares with the clinician 101 a variety of patient data including blood glucose measurements, continuous glucose monitor data, amounts of insulin infused, amounts of food and beverages consumed, exercise schedules, and other lifestyle information. The clinician 101 can obtain additional patient data including measurements of HbA1C, cholesterol levels, triglycerides, blood pressure, and weight of the patient 100. The patient data can be recorded manually or electronically on a handheld diabetes managing device 102, a diabetes analysis software executed on a personal computer (PC) 106, and/or a web-based diabetes analysis site (not shown). The clinician 101 can analyze the patient data manually or electronically using the diabetes analysis software and/or the web-based diabetes analysis site. After analyzing the patient data and reviewing adherence of the patient 100 to previously prescribed therapy, the clinician 101 can decide whether to modify the therapy for the patient 100.

Figure 2:
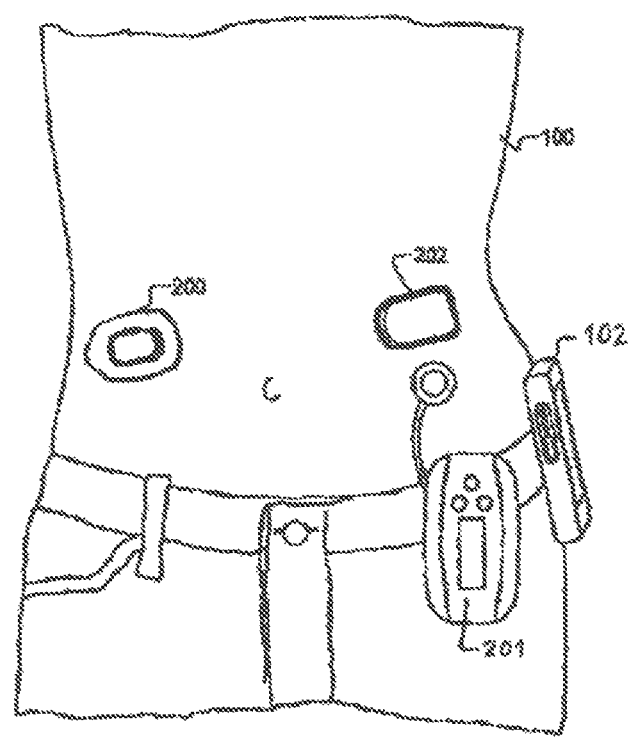
FIG. 2 a schematic representation of a patient with a continuous glucose monitor (CGM), ambulatory durable insulin infusion pump, ambulatory non-durable insulin infusion pump, and diabetes manager, FIG. 3 a schematic representation of a diabetes care system, FIG. 4 a functional block diagram of a diabetes manager, FIG. 5 a functional block diagram of a continuous glucose body fluid, FIG. 6 a graphical representation of results from a clinical study, the results referring to a time lag detected for four identical subcutaneous interstitial glucose sensors each worn by a patient at the same time, FIG. 7 a graphical representation of results from the clinical study, the results referring to a mean time lag of the subcutaneous interstitial sensor of one patient in a study phase A plotted against that in a study phase B, FIG. 8 a graphical representation of results from a clinical study, the results referring to a zero current (offset current) of individual subcutaneous interstitial sensors of various subjects, FIG. 9 a graphical representation of results from a clinical study, the results referring to a mean zero current of the subcutaneous interstitial sensors used measured in both study phases, namely study phase A and B, FIG. 10 a block diagram of a method for determining a continuous body fluid glucose level of a patient, and FIG. 11 a block diagram of an alternative method for determining a continuous body fluid glucose level of a patient.

Referring now to FIG. 2, the patient 100 can use a continuous blood glucose monitor (CGM) 200, an ambulatory durable insulin infusion pump 201 or an ambulatory non-durable insulin infusion pump 202 (collectively insulin pump 201 or 202), and the handheld diabetes managing device 102 (hereinafter the diabetes manager 102). As an alternative, the patient 100 may use an insulin pen or a syringe for administering insulin.

The CGM 200 uses a subcutaneous sensor to sense and monitor the amount of glucose in the subcutaneous fluid of the patient 100 and communicates corresponding readings to the handheld diabetes managing device 102.

The diabetes manager 102 may perform various tasks including measuring and recording blood glucose levels, determining an amount of insulin to be administered to the patient 100 via the insulin pump 201 or 202 or manual insulin injection, receiving patient data via a user interface, archiving the patient data, etc. The diabetes manager 102 periodically receives readings from the CGM 200 indicating a glucose level in the subcutaneous fluid of the patient 100. The diabetes manager 102 may transmit instructions to the insulin pump 201 or 202, which delivers insulin to the patient 100. As an alternative, the diabetes manager 102 may (only) output display signals indicating results of the blood glucose determination.

Insulin can be delivered in the form of a bolus dose, which raises the amount of insulin in the blood of the patient 100 by a predetermined amount. Additionally, insulin can be delivered in a scheduled manner in the form of a basal dose, which maintains a predetermined insulin level in the blood of the patient 100.

Figure 3:
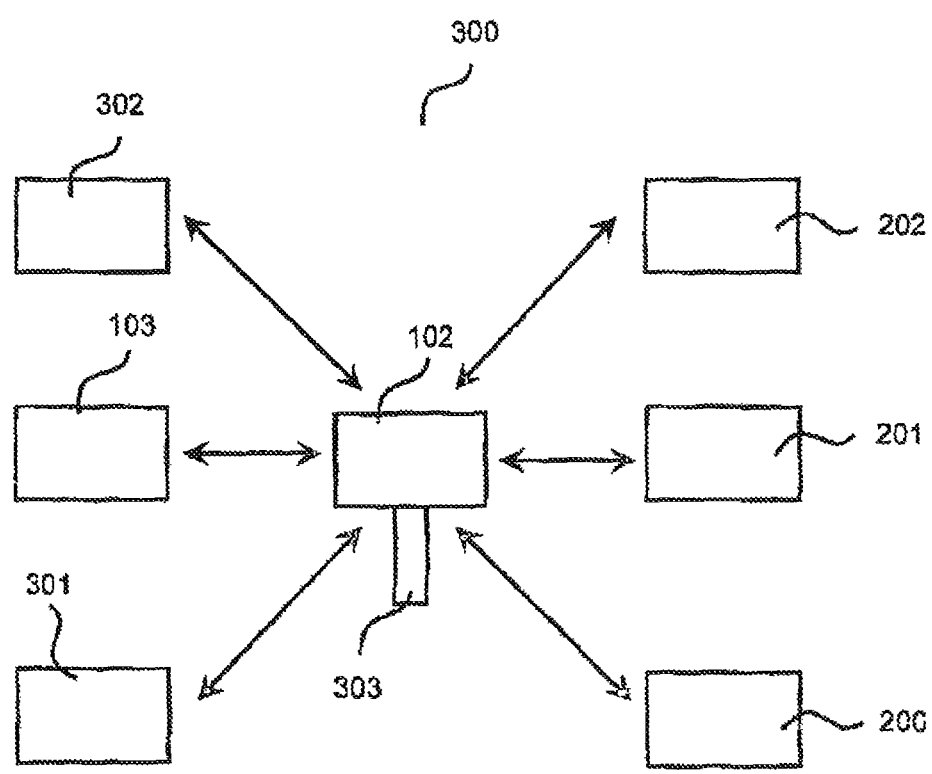

Referring now to FIG. 3, a diabetes management system 300 used by the patient 100 and the clinician 101 includes one or more of the following devices: the diabetes manager 102, the continuous glucose monitor (CGM) 200, the insulin pump 201 or 202, a mobile device 301, the diabetes analysis software on the PC 103, and other healthcare devices 302. The diabetes manager 102 is configured as a system hub and communicates with the devices of the diabetes management system 300. Alternatively, the insulin pump 202 or the mobile device 301 can serve as the system hub. Communication between the various devices in the diabetes management system 300 can be performed using wireless interfaces (e.g., Bluetooth) and/or wireline interfaces (e.g., USB). Communication protocols used by these devices can include, for example, protocols compliant with the IEEE 11073 standard as extended using guidelines provided by Continua® Health Alliance Design Guidelines. Further, healthcare records systems such as Microsoft® HealthVault™ and Google™ Health can be used by the patient 100 and clinician 101 to exchange information.

The diabetes manager 102 can receive glucose readings from one or more sources (e.g., from the CGM 200). The CGM 200 continuously measures the interstitial blood glucose level of the patient 100. The CGM 200 periodically communicates the glucose level to the diabetes manager 102. The diabetes manager 102 and the CGM 200 communicate wirelessly using a proprietary wireless protocol. As an alternative, a standardized protocol for the transmission of CGM data may be applied.

In an embodiment, the diabetes manager 102 may include a blood glucose meter (BGM) and a port that communicates with the BGM (both not shown). The port can receive a blood glucose measurement strip 303. The patient 100 deposits a sample of blood or other bodily fluid on the blood glucose measurement strip 303. The BGM analyzes the sample and measures the blood glucose level in the sample. The blood glucose level measured from the sample and/or the blood glucose level read by the CGM 200 can be used to determine the amount of insulin to be administered to the patient 100.

The diabetes manager 102 communicates with the insulin pump 201 or 202. The insulin pump 201 or 202 can be configured to receive instructions from the diabetes manager 102 to deliver a predetermined amount of insulin to the patient 100. Additionally, the insulin pump 201 or 202 can receive other information including meal and/or exercise schedules of the patient 100. The insulin pump 201 or 202 can determine the amount of insulin to administer based on the additional information.

The insulin pump 201 or 202 can also communicate data to the diabetes manager 102. The data can include amounts of insulin delivered to the patient 100, corresponding times of delivery, and pump status. The diabetes manager 102 and the insulin pump 201 or 202 can communicate using a wireless communication protocol such as Bluetooth. Other wireless or wireline communication protocols can also be used.

In addition, the diabetes manager 102 can communicate with other healthcare devices 302. For example, the other healthcare devices 302 can include a blood pressure meter, a weight scale, a pedometer, a fingertip pulse oximeter, a thermometer, etc. The other healthcare devices 302 obtain and communicate personal health information of the patient 100 to the diabetes manager 102 through wireless, USB, or other interfaces. The other healthcare devices 302 use communication protocols compliant with ISO/IEEE 11073 extended using guidelines from Continual® Health Alliance. The diabetes manager 102 can communicate with the other healthcare devices 302 using interfaces including Bluetooth, USB, etc. Further, the devices of the diabetes management system 300 can communicate with each other via the diabetes manager 102.

The diabetes manager 102 can communicate with the PC 103 using Bluetooth, USB, or other interfaces. A diabetes management software running on the PC 103 may include an analyzer-configurator that stores configuration information of the devices of the diabetes management system 300. The configurator has a database to store configuration information of the diabetes manager 102 and the other devices. The configurator can communicate with users through standard web or computer screens in non-web applications. The configurator transmits user-approved configurations to the devices of the diabetes management system 300. The analyzer retrieves data from the diabetes manager 102, stores the data in a database, and outputs analysis results through standard web pages or computer screens in non-web based applications.

The diabetes manager 102 can communicate with the mobile device 301 using Bluetooth. The mobile device 301 can include a cellular phone, a PDA, or a pager. The diabetes manager 102 can send messages to an external network through the mobile device 301. The mobile device 301 can transmit messages to the external network based on requests received from the diabetes manager 102.

In some embodiments, the CGM 200 measures the level of glucose in the interstitial fluid of the patient 100 by sampling a current. The level of glucose in the interstitial fluid, and therefore the sampled current, is related to the glucose level of the patient 100. In order to accurately estimate the glucose level of the patient 100 based on the interstitial fluid glucose level measured by the CGM 200, the diabetes manager 102 can be periodically calibrated. As an alternative, calibration may be done in a transmitter or control device connected to the subcutaneous sensor. The transmitter or control device may be provided together with the sensor on the patient's skin.

The diabetes manager 102 can be calibrated by determining a calibration equation based on at least one current sample and at least one blood glucose measurement. The current sampled by the CGM 200 and the blood glucose level of the patient 100 can be assumed to have a linear relationship within a normal measurement region of approximately 40 to 400 Milligrams per Deciliter. Based on this assumed linear relationship, the calibration equation can be a linear equation that associates one or more current samples with an estimated glucose level of the patient. After calibration, the diabetes manager 102 can determine an estimated glucose level of the patient 100 based on the calibration equation and the current sampled by the CGM 200.

Figure 4:
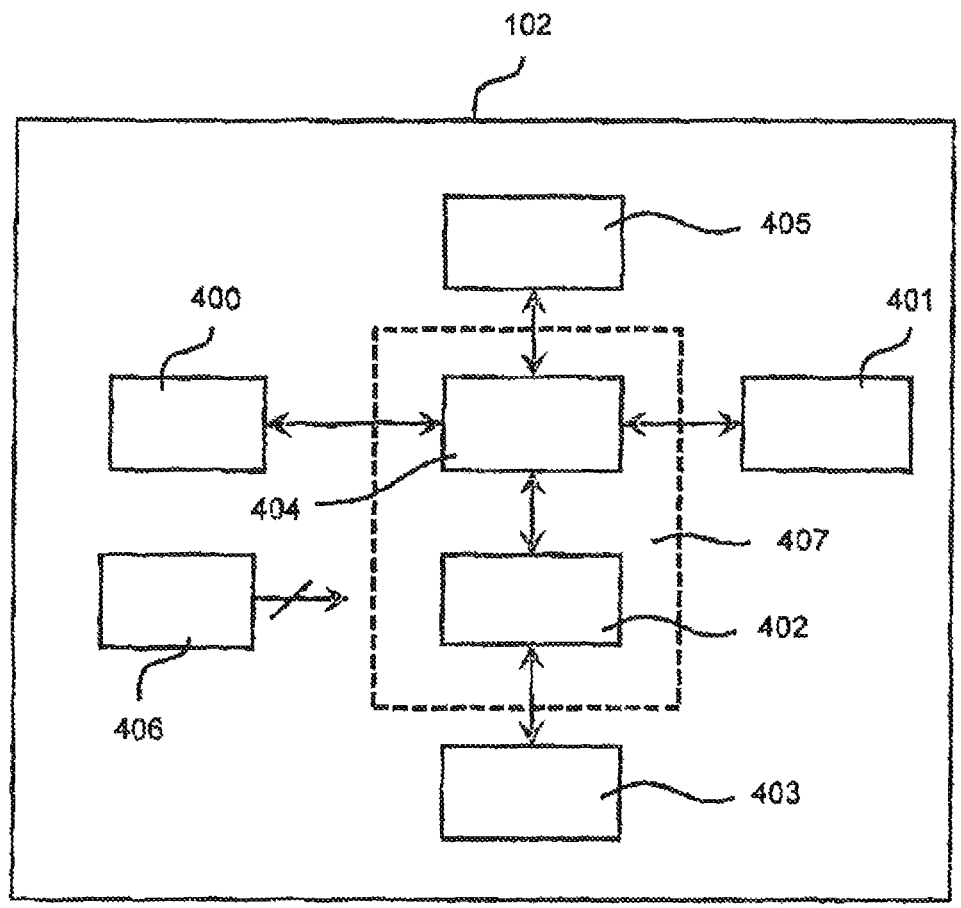

Referring now to FIG. 4, an exemplary diabetes manager 102 includes a blood glucose measuring (BGM) module 400, a communication module 401, a user interface module 402, user interfaces 403, a processing module 404, memory 405, and a power module 406. The user interface module 402 and the processing module 404 can be implemented by an application processing module 407. The BGM module 400 includes a blood glucose measuring engine that analyzes samples provided by the patient 100 on the blood glucose measurement strip 303 and that measures the amount of blood glucose in the samples. The communication module 401 can include multiple radios that communicate with different devices of the diabetes management system 300. The user interface module 402 connects the diabetes manager 102 to various user interfaces 403 that the patient 100 can use to interact with the diabetes manager 102. For example, the user interfaces 403 can include keys, switches, a display, a speaker, a microphone, a secure digital (SD) card port, and/or a USB port (all not shown).

The processing module 404 processes data received from the BGM module 400, the communication module 401, and the user interface module 402. The processing module 404 uses memory 405 for processing and storing data. The memory 405 can include volatile and nonvolatile memory. The processing module 404 outputs data to and receives data from the user interfaces 403 via the user interface module 402. The processing module 404 outputs data to and receives data from the devices of the diabetes management system 300 via the communication module 401. The power module 406 supplies power to the components of the diabetes manager 102. The power module 406 can include a rechargeable battery or other source of power. The battery can be recharged, e.g., by using an adapter that plugs into a wall outlet and/or via a USB port on the diabetes manager 102.

Figure 5:
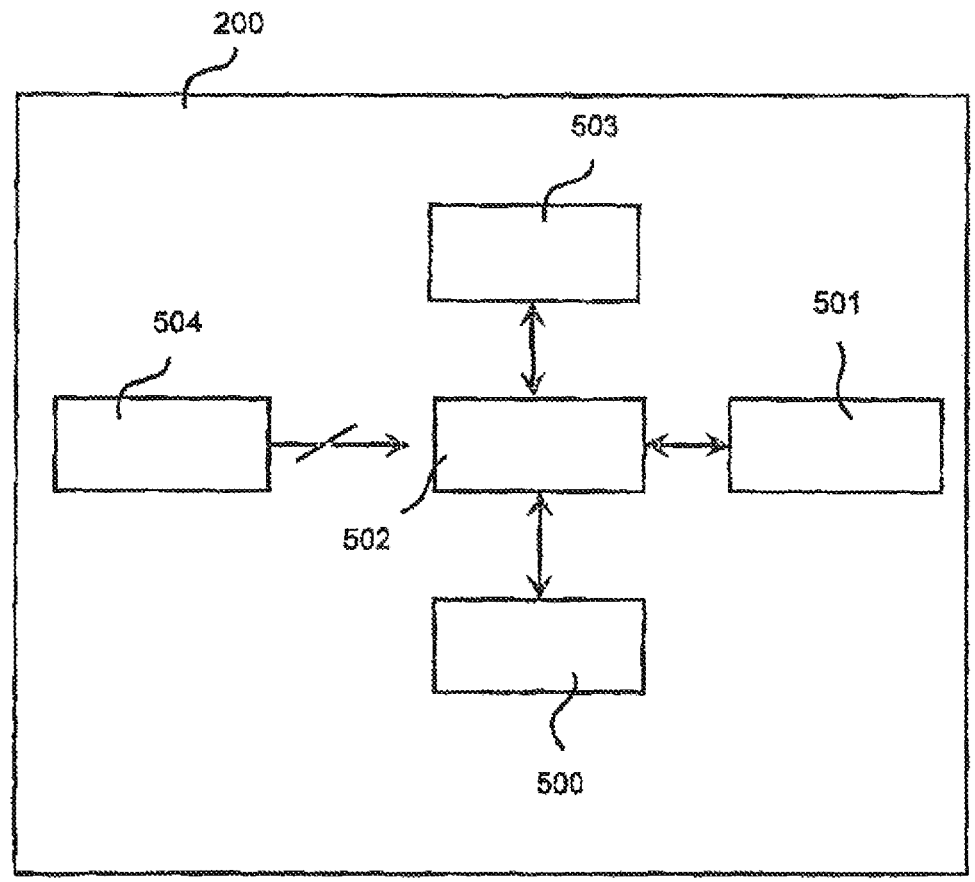

Referring now to FIG. 5, an exemplary continuous glucose monitor (CGM) 200 includes a subcutaneous interstitial sensor 500, a communication module 501, a processing module 502, memory 503, and a power module 504. The continuous glucose monitor (CGM) 200, in alternative embodiment, may also be referred to as system for determining the blood glucose level of a patient. The subcutaneous interstitial sensor 500 can monitor a condition of the patient 100 that is related to the glucose level of the patient 100. For example, the subcutaneous interstitial sensor 500, alone or in combination with processing module 502, periodically samples a current value that corresponds to the level of glucose in the interstitial fluid of the patient 100. The communication module 501 can include one or more radios that communicate with different devices of the diabetes management system 300.

The processing module 502 processes data received from the subcutaneous interstitial sensor 500 and the communication module 501. The processing module 502 uses memory 503 for processing and storing data. The memory 503 can include volatile and nonvolatile memory. The processing module 502 outputs data to and receives data from the devices (for example, diabetes manager 102) of the diabetes management system 300 via the communication module 501. The power module 504 supplies power to the components of the CGM 200. In some embodiments, the power module 504 includes a battery or other source of power. The source of power may include a battery that can be recharged, e.g., by using an adapter that plugs into a wall outlet.

Figure 6:
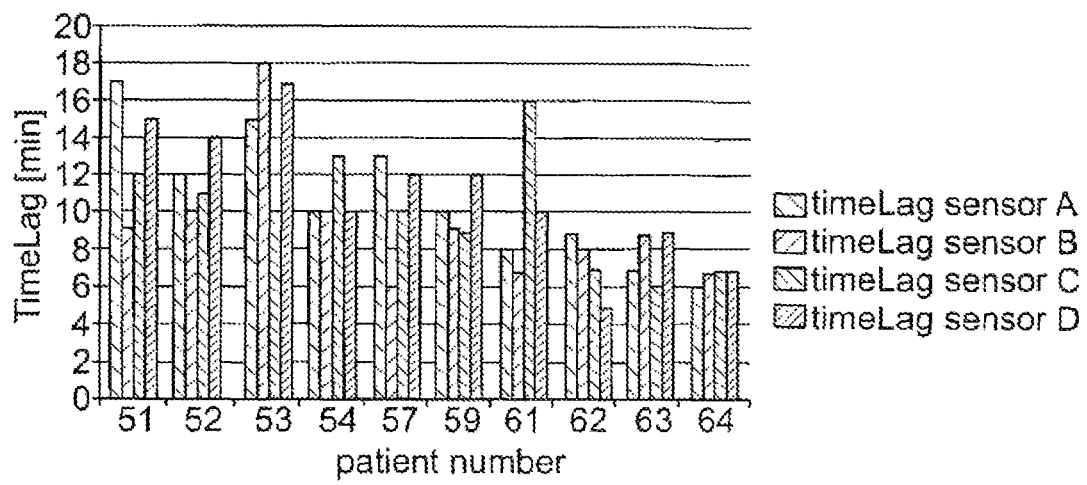
Figure 7:
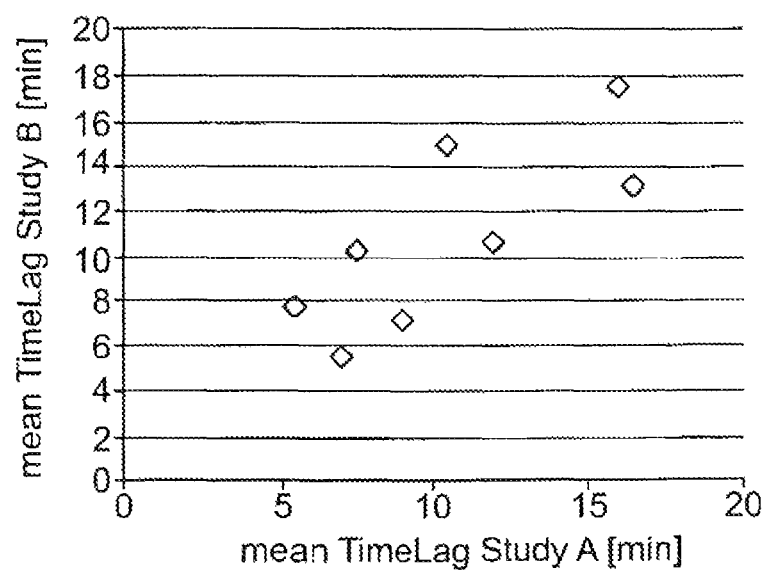

Referring to FIGS. 6 and 7, results of a clinical study are discussed. From the results based on continuous blood glucose measurements using a subcutaneous interstitial glucose sensor it is concluded that there is a patient-specific time lag (time delay) between the glucose level detected by a subcutaneous interstitial sensor and a capillary blood glucose measurement.

FIG. 6 shows the time lag detected for four identical subcutaneous interstitial glucose sensors which were each worn by a patient at the same time in the clinical study. It can be seen that there are patients for whom all four sensors had a low time lag. For other patients the majority of the sensor shows a rather great time lag. A variance analysis has shown that about 50% of the total variability of the time lag (time delay) can be explained by the influence of the patient.

The clinical study was divided into various phases in which identical subcutaneous interstitial sensors were used. Some patients took part in two different study phases.

FIG. 7 shows the mean time lag of the sensor of one patient in study phase A plotted against that in study phase B (each point thus represents one patient who participated twice). The study phases were conducted at least eight months apart. FIG. 7 shows a strong correlation of the mean time lags of a patient in both study phases (i.e. in the two study phases separated from each other by more than eight months in time, some patients has small time lag, others a large time lag). The patient-specific time lag or delay therefore remained stable in these patients over at least three-quarters of a year. Overall the evaluations of the study data show that there is a patient-specific component of the time lag and that this remains stable over a long period of time.

This conclusion can be utilised for correcting the time lag in the process of determining the blood glucose level for a patient in a continuous measurement, e.g. for (partially) correcting the time lag or for the prediction/warning of hypoglycaemia, but a patient-specific one. In the example of a time lag correction shown above, an individual (personalised) time lag $\Delta t$(personal) would be used instead of a general (mean) time lag applied for a whole group of patients.

In order to be able to use a patient-specific time lag, this is to be individually determined on the patient. To do this, in a retrospective analysis the blood glucose measurements are offset in time against the sensor signal within predetermined limits, e.g. from −40 to +40 minutes in 1 minute increments, and a correspondence criterion between the course of the blood glucose determined from capillary blood glucose determination and the signal of the subcutaneous interstitial sensor is determined. The time offset at which the correspondence criterion provides the best values, is defined as the time lag between the blood glucose determined by capillary blood analysis and the signal received from the subcutaneous interstitial sensor. An example of the correspondence criterion is the correlation coefficient which can be used both with the sensor raw signal and also the calibrated sensor signal (i.e. the sensor glucose). At the time offset with the best correspondence of capillary blood glucose and sensor signal the correlation coefficient is at a maximum. An alternative, which specifically works with a calibrated sensor signal, is the MARD (Mean Absolute Relative Difference), which is minimal at best correspondence. In addition, all other criteria for measuring the similarly of two time lines can be used.

Measurement of the time lag presupposes that that the blood glucose concentration changes over time, as only then does a time lag become evident. The measurement is more reliable, the greater the blood glucose changes are and the more glucose measurements from capillary blood are available during the change phase. At the same time the CGM signal provided by the subcutaneous interstitial sensor also has to be recorded. For practical application this means that before using a personal time lag, a patient must experience significant blood glucose rises within a few days while wearing a CGM sensor. It may be recommendable for several glucose increases to be carried out on several days and carry out the correspondingly frequent capillary blood glucose measurements. This thus determined personalised time delay (time lag) can then be used as input for all algorithms for evaluating or improving the sensor signal that make use of an assumed time lag. It is advantageous to repeat such measurement of the time lag at greater time intervals in order to detect changes in the personal time lag (conceivable, for example, through major changes in lifestyle, considerable changes in weight etc.).

In an alternative embodiment, the patient-specific time delay or lag may be determined in an estimation process. One or more of the following estimators may be applied: Pearson correlation coefficient; Spearman correlation coefficient; Pearson correlation coefficient of log transformed blood analyzer reference measurements (e.g. obtained from analyzers from YSI) and CGM data; R-squared statistics of certain form transformed linear regression, defined as Agreement Criterion (AC), Root Mean Square Coefficient of Variation, Root Mean Squared Error Percent and/or Mean Absolute Relative Difference (MARD). Detailed formulas of these estimator may be found in "Diabetes research and Clinical Practice, 87 (2010), 348-353; Garg et al.; Time lag characterization of two continuous glucose monitoring systems" and the appendix cited therein.

If the personalised time lag is known, it can also be assessed whether a CGM system is suitable for this patient. This applies in particular to the reliability in terms of the timing of a time-critical hyper- or hypoglycaemia warning or for controlling insulin pumps as part of artificial pancreas function. A time lag of more than 20 minutes can, for example, lead to unreliable functioning of the CGM-based system—even if the system is reliably measuring the interstitial glucose concentration.

In addition, in a clinical study it has been found that there is a patient-specific in-vivo zero sensor current of the subcutaneous interstitial sensor, the zero sensor current referring to a detected sensor signal which is present independently of the glucose level of the bodily fluid under investigation.

Figure 8:
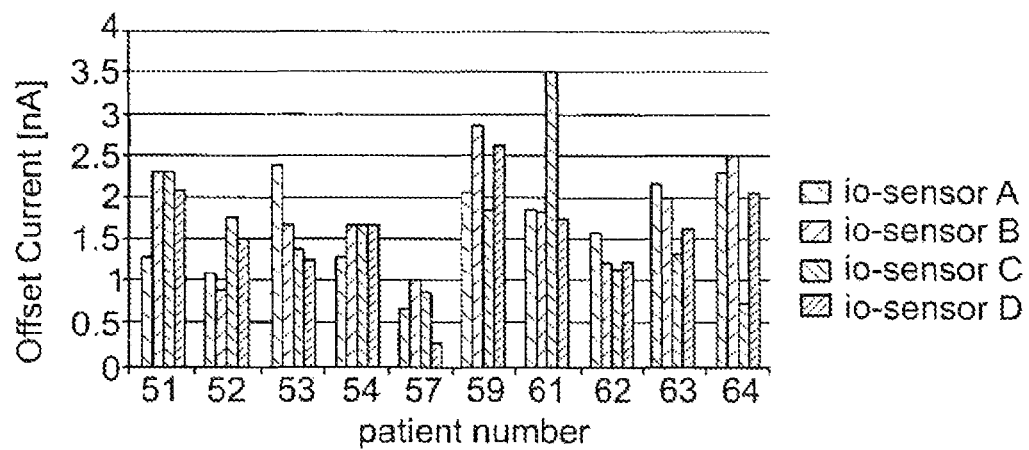
Figure 9:
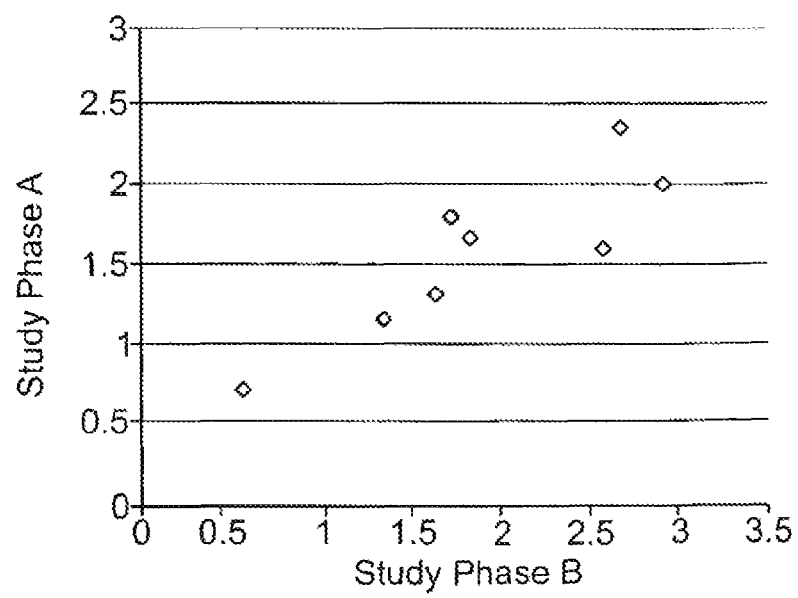

In a similar way, the data of clinical study have shown that in particular the zero current of the subcutaneous interstitial sensor (i.e. the glucose-independent portion of the sensor current) is patient-specific. FIG. 8 shows the zero currents (offset current) of the individual sensors of various subjects in the study phase (four simultaneously operating sensors per subject). For subjects who took part in two study phases at an interval of more than eight months, FIG. 9 again shows the mean zero currents of the sensors used measured in both study phases. For determining the personalised zero current, frequent in-vivo measurements of the blood glucose together with the use of a CGM system are also necessary. Here too it is advantageous to considerably vary the concentration of blood glucose, as in this case the (retrospective) determination of zero current and sensitivity becomes more reliable.

Figure 10:
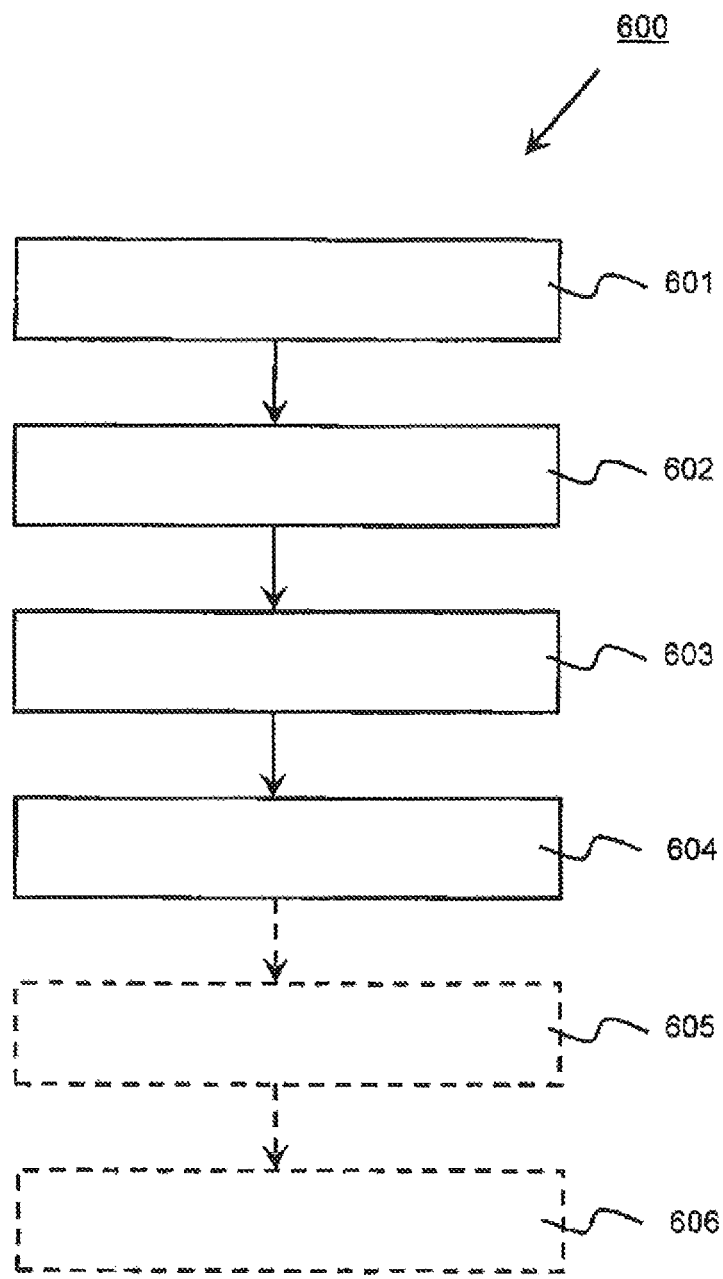

Referring to FIG. 10, an exemplary method 600 for continuously determining a body fluid glucose level of a patient is illustrated. The method 600 begins at step 601 where a present sensor signal is detected at a measuring time tm in a present continuous interstitial blood glucose measurement for a patient. In step 602, in a data processing unit measurement data are received, the measurement data representing the present sensor signal. The data processing unit, for example, may be provided in the handheld diabetes management device 102 or the continuous glucose monitor 200. The processing module 404 or 502 may be provided with the data processing unit. The measurement data received are indicative of a continuous sensor signal provided by a glucose sensor element such as subcutaneous interstitial sensor 500.

In the data processing unit, also, in step 603 time delay data are provided. For the patient, the time delay data are representing a patient-specific time delay $\Delta t$ ($\Delta t$(personal)) between a blood glucose value measured in a continuous interstitial blood glucose measurement and a blood glucose reference value measured in a capillary blood glucose measurement in the data processing system, the blood glucose value and the blood glucose reference value referring to the patient's same blood glucose level. As an alternative or in addition, at least one of sensor offset data representing, for the patient, a patient-specific sensor signal offset for the sensor, and sensor sensitivity data representing, for the patient, a patient-specific sensor sensitivity for the sensor may be provided in the data processing unit. At least one of the time delay data, the sensor offset data, and the sensor sensitivity data may also be referred to as sensor signal correction data.

Following, in step 604 blood glucose level data are provided in the data processing unit, the blood glucose level data representing, for example, a previous blood glucose level of the patient at a previous time tpr=tm−$\Delta t$ by determining a blood glucose value from the measurement data and assigning the blood glucose value to the previous time tpr in the data processing system. For determining corrected measurement data from the measurement data, in addition or as an alternative, the measurement data may be corrected by applying at least one of the sensor signal correction data, and determining a blood glucose level for the patient from the corrected measurement data.

Further, in the data processing system rate of change data representing a rate of change of the blood glucose level of the patient may be provided (step 605). Following, in step 606 present blood glucose level data representing a present blood glucose level of the patient at the measuring time tm may be provided by determining a present blood glucose value from the blood glucose value at the previous time tpr and the rate of change of the blood glucose level. The rate of change indicates the change of the patient's blood glucose level over time. This information can be used for determining the change over a time period from tpr to tm. Starting from the blood glucose level at the previous time tpr, the blood glucose level of the patient at the present time tm is determined.

Figure 11:
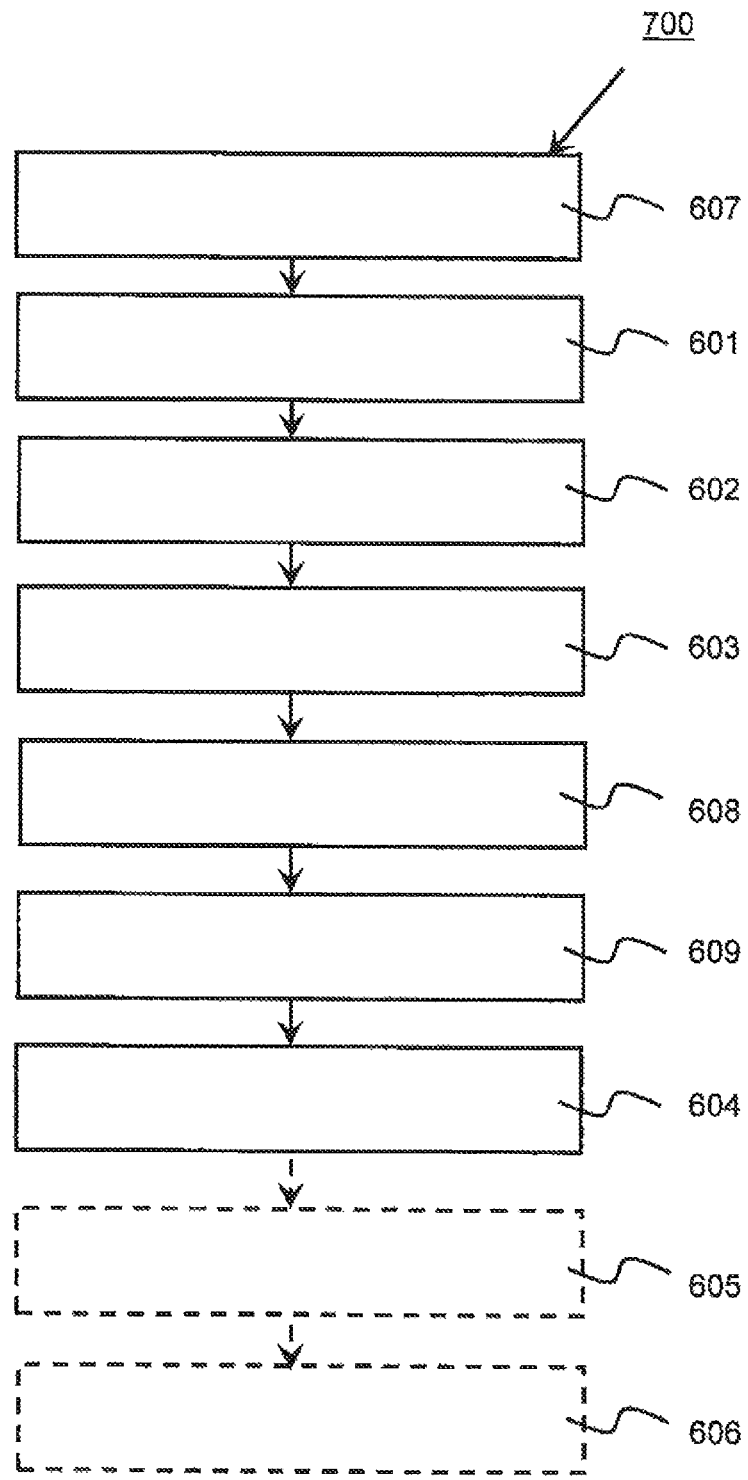

FIG. 11 shows an alternative method 700 for continuously determining a body fluid glucose level of a patient. Referring to FIGS. 10 and 11, the alternative method according to FIG. 11 further comprises a step 607 of providing pre-set sensor signal correction data in a memory device of the system for determining the blood glucose level, e.g. in the memory 503 connected to the processing module 502. The pre-set sensor signal correction data are representing, for the sensor, e.g. the subcutaneous interstitial sensor 500, a pre-set sensor-specific signal correction. The pre-set sensor signal correction data comprise at least one of pre-set sensor offset data, and pre-set sensor sensitivity data. In step 608 it is determined whether the sensor signal correction data provided, for example, in step 603 are different from the pre-set sensor signal correction data.

The sensor signal correction data are applied to the present sensor signal if the sensor signal correction data are determined to be different from the pre-set sensor signal correction data, otherwise the pre-set sensor signal correction data are applied to the present sensor signal.

The pre-set sensor signal correction data may provide for sensor-specific parameters characterizing individual characteristics of the sensor to be used for the measurement. The pre-set sensor signal correction data may be stored in the memory prior to the measurement, e.g. in the course of a calibration process or at the time of connecting the sensor to the system for determining the blood glucose level.

The determining whether the sensor signal correction data are different from the pre-set sensor signal correction data in step 608 may comprise determining a difference value for the sensor signal correction data and the pre-set sensor signal correction data, and determining the sensor signal correction data to be different from the pre-set sensor signal correction data if the difference value is equal to or bigger than a pre-set difference value. The pre-set difference value may be a relative value identifying a relative difference between the data, e.g. the pre-set difference value may be provided as percent value. For example, the pre-set difference value may identify a value of 10%, indicating that the sensor signal correction data shall be determined different from the pre-set sensor signal correction data if there is a difference of at least 10%. As an alternative, the pre-set difference value may identify a value of 20%.

The method may further comprise, if the sensor signal correction data are determined to be different from the pre-set sensor signal correction data, replacing the pre-set sensor signal correction data in the memory device by the sensor signal correction data in the memory device in step 609. The pre-set sensor signal correction data may be overwritten by the sensor signal correction data in the memory. The replacing may apply to at least one of the pre-set sensor offset data, and the pre-set sensor sensitivity data. In a similar way pre-set patient-specific time delay may be stored in the memory, but overwritten afterwards, e.g. during a measurement process and/or a (additional) calibration process.

As an alternative or in addition, the patient-specific sensor signal offset and/or the patient-specific sensor sensitivity may be corrected for in the course of determining the blood glucose level from the measured sensor signals.

The invention claimed is:

1. A method for determining a blood glucose level for a patient, the method comprising, in a system for determining the blood glucose level for the patient,
   detecting a present sensor signal at a measuring time tm in a present continuous interstitial blood glucose measurement for the patient;
   providing measurement data representing the present sensor signal;
   providing patient-specific sensor signal correction data representing, for the patient, a patient-specific signal correction, the patient-specific sensor signal correction data being determined from a former interstitial blood glucose measurement for the patient and comprising patient-specific time delay data representing, for the patient, a patient-specific time delay Δt between a blood glucose value measured in a continuous interstitial blood glucose measurement and a blood glucose reference value measured in a capillary blood glucose measurement, the blood glucose value and the blood glucose reference value referring to the same blood glucose level;
   providing pre-set sensor signal correction data in a memory device of the system for determining the blood glucose level, the pre-set sensor signal correction data representing, for a sensor, a pre-set sensor-specific signal correction, the pre-set sensor signal correction data being selected from the group consisting of pre-set sensor offset data and pre-set sensor sensitivity data;
   determining whether the patient-specific sensor signal correction data are different from the pre-set sensor signal correction data; and
   determining corrected measurement data representing a corrected present sensor signal by applying:
      the patient specific sensor signal correction data to the present sensor signal if the patient specific sensor signal correction data are determined to be different from the pre-set sensor signal correction data; or
      the pre-set sensor signal correction data to the present sensor signal if the patient specific sensor signal correction data are determined not to be different from the pre-set sensor signal correction data;
   wherein the applying is further comprising:
      determining blood glucose level data representing a previous blood glucose level of the patient at a previous time tpr=tm−Δt by determining a blood glucose value from the measurement data and assigning the blood glucose value to the previous time tpr;
      providing rate of change data representing a rate of change of the blood glucose level of the patient; and
      providing present blood glucose level data, representing a present blood glucose level of the patient at the measuring time tm by determining a present blood glucose value from the blood glucose value at the previous time tpr and the rate of change of the blood glucose level: and
   determining the blood glucose level for the patient from the corrected measurement data.

2. A method for determining a blood glucose level for a patient, the method comprising, in a system for determining the blood glucose level for the patient,
   detecting a present sensor signal at a measuring time tm in a present continuous interstitial blood glucose measurement for the patient;
   providing measurement data representing the present sensor signal;
   providing patient-specific sensor signal correction data representing, for the patient, a patient-specific signal correction, the patient-specific sensor signal correction data being determined from a former interstitial blood glucose measurement for the patient and comprising patient-specific, time delay data representing, for the patient, a patient-specific time delay Δt between a blood glucose value measured in a continuous interstitial blood glucose measurement and a blood glucose reference value measured in a capillary blood glucose measurement, the blood glucose value and the blood glucose reference value referring to the same blood glucose level;
   providing pre-set sensor signal correction data in a memory device of the system for determining the blood glucose level, the pre-set sensor signal correction data representing, for a sensor, a pre-set sensor-specific signal correction, the pre-set sensor signal correction data being selected from the group consisting of pre-set sensor offset data and pre-set sensor sensitivity data:
   determining whether the patient-specific sensor signal correction data are different from the pre-set sensor signal correction data: and
   determining corrected measurement data representing a corrected present sensor signal by applying;
      the patient specific sensor signal correction data to the present sensor signal if the patient specific sensor signal correction data, are determined to be different from the pre-set sensor signal correction data; or the pre-set sensor signal correction data to the present sensor signal if the patient specific sensor signal correction data are determined not to be different from the pre-set sensor signal correction data;

wherein the applying is further comprising:
  determining blood glucose level data representing a previous blood glucose level of the patient at a previous time tpr=tm−Δt by determining a blood glucose value from the measurement data and assigning the blood glucose value to the previous time tpr;
  providing rate of change data representing a rate of change of the blood glucose level of the patient; and
  providing future blood glucose level data representing a future blood glucose level of the patient at a future time tf=tm+Δt by determining a future blood glucose value from the blood glucose value at the previous time tpr and the rate of change of the blood glucose level; and
  determining the blood glucose level for the patient from the corrected measurement data.

3. Method according to claim 2, further comprising providing present blood glucose level data representing a present blood glucose level of the patient at the measuring time tm by determining a present blood glucose value from the blood glucose value at the previous time tpr and the rate of change of the blood glucose level.

4. Method according to claim 1 or 2, wherein the applying further comprises subtracting the pre-set sensor offset from the present sensor signal.

5. Method according to claim 1 or 2, further comprises
  determining a difference value for the patient-specific sensor signal correction data and the pre-set Sensor signal correction data; and
  determining the patient-specific sensor signal correction data to be different from the pre-set sensor signal correction data if the difference value is equal to or bigger than a pre-set difference value.

6. Method according to claim 5, further comprising, if the patient-specific sensor signal correction data are determined to be different from the pre-set sensor signal correction data, replacing the pre-set sensor signal correction data by the patient-specific sensor signal correction data in the memory device.

7. Method according to claim 1 or 2, further comprising, if the patient-specific sensor signal correction data are determined to be different from the pre-set sensor signal correction data, replacing the pre-set sensor signal correction data by the patient-specific sensor signal correction data in the memory device.

8. A system for determining a blood glucose level for a patient, comprising:
  a blood glucose measurement device configured to detect a present sensor signal at a measuring time tm in a present continuous interstitial blood glucose measurement for the patient, and
  a blood glucose analyzing device, comprising a data processing device, configured to provide:
    measurement data representing the present sensor signal;
    patient-specific sensor signal correction data representing, for the patient, a patient-specific signal correction, the patient-specific sensor signal correction data being determined from a former interstitial blood glucose measurement for the patient and comprising patient-specific time delay data representing, for the patient, a patient-specific time delay Δt between a blood glucose value measured in a continuous interstitial blood glucose measurement and a blood glucose reference value measured in a capillary blood glucose measurement, the blood glucose value and the blood glucose reference value referring to the same blood glucose level:
    corrected measurement data representing a corrected present sensor signal by applying sensor signal correction data to the present sensor signal; and
    the blood glucose level for the patient from the corrected measurement data, wherein the data processing device includes a memory device including pre-set sensor signal correction data for determining the blood glucose level, the pre-set sensor signal correction data representing, for a sensor, a pre-set sensor-specific signal correction, the pre-set sensor signal correction data being selected from the group consisting of pre-set sensor offset data and pre-set sensor sensitivity data, wherein the data processing device is further configured, in the applying, to:
  determine if the patient-specific sensor signal correction data are different from the pre-set sensor signal correction data, and
  apply the patient specific sensor signal correction data to the present sensor signal if the patient specific sensor signal correction data are determined to be different from the pre-set sensor signal correction data, or
  apply the pre-set sensor signal correction data to the present sensor signal if the patient specific sensor signal correction data are determined not to be different from the pre-set sensor signal correction data;

the data processing device further being configured to:
determine blood glucose level data representing a previous blood glucose level of the patient at a previous time tpr=tm−Δt by determining a blood glucose value from the measurement data and assigning the blood glucose value to the previous time tpr;
provide rate of change data representing a rate of change of the blood glucose level of the patient; and
at least one of the following:
  provide present blood glucose level data representing a present blood glucose level of the patient at the measuring time tm by determining a present blood glucose value from the blood glucose value at the previous time tpr and the rate of change of the blood glucose level; and
  provide future blood glucose level data representing a future blood glucose level of the patient at a future time tf=tm+Δt by determining a future blood glucose value from the blood glucose value at the previous time tpr and the rate of change of the blood glucose level.

* * * * *